United States Patent [19]

Strom

[11] Patent Number: 4,934,523

[45] Date of Patent: Jun. 19, 1990

[54] DENTAL FLOSS CONTAINER

[76] Inventor: Paul H. Strom, 1123 Kriebel Mill Rd., Collegeville, Pa. 19426

[21] Appl. No.: 396,305

[22] Filed: Aug. 21, 1989

[51] Int. Cl.$^5$ ............................................. A61B 19/02
[52] U.S. Cl. .................................. 206/63.5; 206/63.3; 206/368; 206/409; 132/326
[58] Field of Search ...................... 206/63.3, 63.5, 389, 206/368, 409, 603; 132/323, 324, 326, 327

[56] References Cited

U.S. PATENT DOCUMENTS

| | | | |
|---|---|---|---|
| 2,617,559 | 11/1952 | Van Der Spek | 206/603 |
| 3,163,288 | 12/1964 | Arvidsson | 206/63.3 |
| 3,871,393 | 3/1975 | Wharton | 132/326 |
| 3,890,986 | 6/1975 | Gerlich | 206/63.3 |
| 3,924,647 | 12/1975 | Lindblad | 132/326 |
| 4,034,770 | 7/1977 | Trecker | 206/63.5 |
| 4,084,692 | 4/1978 | Bilweis | 206/63.3 |
| 4,327,755 | 5/1982 | Endelson | 206/63.5 |
| 4,495,957 | 1/1985 | Beggs et al. | 132/326 |
| 4,582,196 | 4/1986 | Hughson et al. | 206/63.3 |
| 4,693,365 | 9/1987 | Corella | 206/63.5 |

*Primary Examiner*—David T. Fidei
*Attorney, Agent, or Firm*—Leon Gilden

[57] ABSTRACT

A heat or adhesively sealed envelope containing a coiled predetermined length of dental floss is set forth. Alternatively, a dental floss container is provided wherein a continuous groove is formed within a side and forward wall of the container that merge at a common intersection. Dental floss contained within the container includes an exterior poriton provided with an adhesive strip fixedly secured to the exterior portion of the dental floss to provide a manual securement member to enhance grasping of the dental floss by an individual.

3 Claims, 1 Drawing Sheet

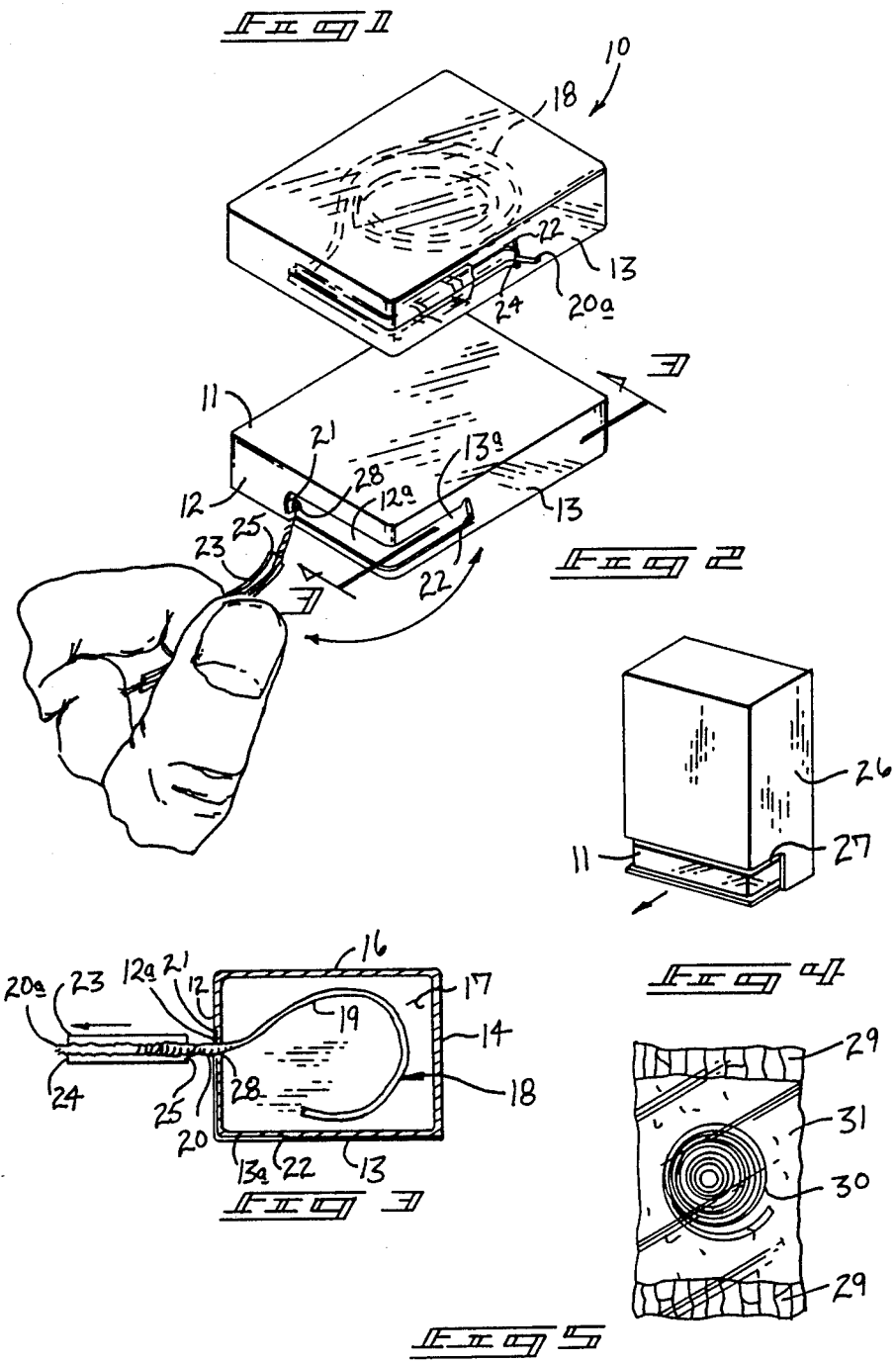

DENTAL FLOSS CONTAINER

BACKGROUND OF THE INVENTION

1. Feild of the Invention

The field of invention relates to dental floss, and more particular dental floss container wherein the same sets forth hermetically sealed individual portions of dental floss.

2. Description of the Prior Art

The use of dental floss and containers therefore are well known in the prior art. It has heretofore been inconvenient for dental floss to be transported by an individual in bulk as such bulk containers are frequently awkward to confine upon the person of an individual. Attempts to provide dental floss for individual use has been set forth by the prior art and may be found, for example, in U.S. Pat. No. 2,180,522 to Henne setting forth a throw-away dental floss unit where an individual portion of dental floss is strung between extremities of a framework. The Henne patent does not provide for the sanitized portage and containment of individual dental floss portions, as set forth by the instant invention.

U.S. Pat. No. 2,909,277 to Thiers, et al., sets forth a dental floss dispenser utilizing a plurality of strands of dental floss for individual use. The Thiers patent, while of interest relative to the dispensing of individual portions of dental floss, fails to provide the ease and sanitary containment of individual portions of dental floss, as set forth by the instant invention.

U.S. design patent No. 259,365 to Petrobic; U.S. design patent No. 264,758 to Walker; and U.S. design patent No. 266,194 to Graves sets forth individual-type dental floss portions, but is of a construction relatively remote from that of the instant invention, but of interest relative to note the development of individual dental floss organizations.

As such, it may be appreciated that there is a continuing need for a new and improved dental floss container wherein the same addresses both the problems of sanitary containment and ease of use of dental floss within such a container.

SUMMARY OF THE INVENTION

In view of the foregoing disadvantages inherent in the known types of individual dental floss organizations now present in the prior art, the present invention provides a dental floss container wherein the same hermetically seals an individual portion of dental floss within a container and further provides for an enhanced manual grasping member for a securement of the dental floss by an individual. As such, the general purpose of the present invention, which will be described subsequently in greater detail, is to provide a new and improved dental floss container which has all the advantages of the prior art individual dental floss portions and none of the disadvantages.

To attain this, the present invention comprises a hermetically sealed envelope utilizing adhesive or heat sealing of a polymeric paper covering sealing a predetermined length of dental floss therein. Alternatively, a container comprising opposed side and end walls. A continuous groove is formed within an adjacent forward and side wall with an aperture positioned approximate a rearward end of the groove for withdrawal of an individual portion of dental floss contained therein. An exterior portion of the dental floss includes a flexible adhesive strip fixedly secured to the dental floss whereupon the adhesive strip is initially secured within the groove and is of a length substantially equal to that and of complementary configuration to the groove whereupon removal of the flexible strip from the groove provides for a manual grasping member for securement of the dental floss in use.

My invention resides not in any one of these features per se, but rather in the particular combination of all of them herein disclosed and claimed and it is distinguished from the prior artt in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regared as including such equivalent constructions insofar as they do not depart from the spirit an scope of the present invention.

Further, the purpose of the foregoing abstract is to enable the U.S. Patent and Trademark Office and the public generally, and espcially the scientists, engineers and practitioners in the art who are not familiar with. patent or legal terms or phraseology, to determine qucikly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental floss container which has all the advantages of the prior art dental floss containers and none of the disadvantages.

It is another object of the present invention to provide a new and improved dental floss container which may be easily and efficiently manufactured and marketed.

It is a further object of the present invention to provide a new and improved dental floss container which is of a durable and reliable construction.

An even further object of the present invention is to provide a new and improved dental floss container which is susceptible of a low cost of manufacture with regard to both materials and labor, and which accordingly is then susceptible of low prices of sale to the consuming public, thereby making such dental floss containers econmically available to the buying public.

Still yet another object of the present invention is to provide a new and improved dental floss container which provides in the apparatuses and methods of the prior art some of the advantages thereof, while simultaneously overcoming some of the disadvantages normally associated therewith.

Still another object of the present invention is to provide a new and improved dental floss container wherein the same provides for dispensing of individual containers of dental floss contained therewithin and further provides for an enhanced manual grasping member hermetically sealing the dental floss to the container.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the container of the instant invention.

FIG. 2 is an isometric illustration of the container of the instant invention with the dental floss being withdrawn therefrom FIG. 3 is an orthographic view, taken along the lines 3—3 of FIG. 2, in the direction indicated by the arrows.

FIG. 4 is an isometric illustration of a typical dispenser for use in combination with the container of the instant invention.

FIG. 5 is an orthographic top plan view of a sealed package containing a coiled length of dental floss.

DESCRIPTION OF THE PREFERRED EMBODIMENT

With reference now to the drawings, and in particular to FIGS. 1 to 4 thereof, a new and improved dental floss container embodying the principles and concepts of the present invention and generally designated by the reference numeral 10 will be described.

More specifically, the dental floss container 10 of the instant invention essentially comprises a flexible dental floss package 11 including a forward wall 12 spaced forwardly of a rear wall 14 and a right side wall 13 spaced from a left side wall 15 to define an enclosed package 11 with a top wall 16 overlying a bottom wall 17. A predetermined length of dental floss 18 is randomly positioned within the package 11, as it is contemplated that the package 11 be heremetically sealed to ensure a sanitized portion of dental floss for ultimate use by an individual. The dental floss 18 includes an interior portion of dental floss 19 extending from an interior portion of the package to an exterior portion of dental floss 10 positioned exteriorly of the package with the interior portion of the dental floss 19 communicating with the exterior portion 20 means of a through-extending aperture 28 formed through the forward wall 12 of the package. More specifically, the aperture 28 extends through a forward wall groove 12a communicating with a right side wall groove 13a to define the continuous groove within forward and right side walls of the package 11. The groove is formed with a forward groove edge 22 positioned adjacent the aperture 28 within the forward wall 12 and extending about the package to end in a forward groove edge 22 defining the forwardmost extent of the groove within the right side wall 13. An adhesive flexible strip 23 is of a complementary configuration and geometry to be received within the aforenoted groove with the adhesive flexible strip defining a forward edge 24 and a rear edge 25 to respectively abut the rear groove edge 21 and the forward groove edge 22 respectively when the adhesive strip 23 is positioned within the groove. The exterior portion of the dental floss 20 terminates in a forward tip 20a that extends forwardly of the forward edge 24 of the flexible strip 23 to provide a gasping position for manual securement by an individual when withdrawal of the dental floss from interiorly of the package 11 is desired.

It is to be understood that the adhesive flexible strip 23, when secured within the groove, maintains the dental floss 18 in a hermetically sealed relationship within the package 11 and the exterior portion of the dental floss 20 is shielded from contamination by the overlapping arrangement of the adhesive strip 23. The adhesive strip 23 is integrally and fixedly secured to the dental floss and remains on the dental floss when the dental floss is removed from the package whereby the adhesive flexible strip 23 is utilized as a manual grasping member to enhance grasping of the dental floss 18 is use.

The dental floss 18 utilizfed is provided in either unwaxed or waxed relationship and to this end, the package 11 is color-coded in a first coloration to define an unwaxed portion of dental floss and in a second coloration to define a waxed configuration of dental floss 18.

It is contemplated that a series of packages 11 be provided within a dispensing carton 26, as illustrated in FIG. 4, with an underlying slot 27 to enable manual grasping of each individual package 11 and withdrawal from the dispensing carton 26.

FIG. 5 is illustrative of an embodiment of the instant invention wherein a flexible polymeric or fibrous envelope 31 defined by a continously encircling body portion and heat sealed or alternatively adhesively sealed at remote ends 29 to sealingly encompass a predetermined length of dental floss 30 therein. The envelope 31 is of a compact conventional configuration enabling ease of storage, transport, and dispensing thereof.

The manner of usage and operation of the instant invention should be understood from the above disclosure and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and descirbed in the specification are intended to be encompassed by the present invention.

Therefore, the foregoing is considered as illustrative only of the priciples of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A dental floss container for sanitary support and dispensing of a predetermined length of dental floss contained therein comprising, a flexible package defined by a top wall, a bottom wall underlying and spaced from said top wall, a forward wall with a rear wall spaced from said forward wall,
and
a right side wall and a left side wall spaced from said right side wall;
said right side wall intersecting said forward wall to define a corner of said package with a length of dental floss including a first length positioned within said package extending exteriorly of said package to a second length overlying said forward wall and said corner,
and
securement means securing said second length of dental floss to said forward wall and said corner.
and
wherein said second length of dental floss overlies said right side wall,
and
wherein said right side wall and said forward wall further include a continuous elongate groove formed in said forward wall and said right side wall with said second length of dental floss positioned within said groove, and a forward tip of said second length of dental floss extending beyond said groove,
and
further including an adhesive flexible strip integrally secured to said second length of dental floss wherein said adhesive flexible strip is of a first configuration of complementary shape to a second configuration defined by said groove.

2. A dental floss container as set forth in claim 1, wherein said first length of dental floss communicates with said second length of dental floss through an aperture positioned within said groove and wherein said aperture is positioned adjacent a rear groove edge formed within said forward wall.

3. A dental floss container as set forth in claim 2, wherein said package comprises a package of a first coloration when said predetermined length of dental floss is unwaxed and wherein said package is of a second coloration when said dental floss is waxed throughout its length.

* * * * *